(12) United States Patent
Shroff et al.

(10) Patent No.: US 6,831,179 B2
(45) Date of Patent: Dec. 14, 2004

(54) PROCESS FOR THE STEREOSELECTIVE PREPARATION OF INSECTICIDE 6,7,8,9,10-10-HEXAHALO-1,5,5A,6,9,9A-HEXADRO-6,9-METHANO-2,4,3-BENZODIOXATHIEPIN-3-OXIDE

(75) Inventors: Ashwin Champraj Shroff, Maharashtra (IN); Abhijit Premvallabh Purohit, Maharashtra (IN); Sanjay Dhirajlal Vadodaria, Maharashtra (IN)

(73) Assignee: Excel Industries Limited, Mumbai (IN)

(*) Notice: Subject to any disclaimer, the term of this patent is extended or adjusted under 35 U.S.C. 154(b) by 0 days.

(21) Appl. No.: 10/474,029

(22) PCT Filed: Apr. 24, 2001

(86) PCT No.: PCT/IN01/00092

§ 371 (c)(1),
(2), (4) Date: Oct. 10, 2003

(87) PCT Pub. No.: WO02/085884

PCT Pub. Date: Oct. 31, 2002

(65) Prior Publication Data

US 2004/0092751 A1 May 13, 2004

(51) Int. Cl.⁷ .............................................. C07D 333/50
(52) U.S. Cl. ........................................................ 549/10
(58) Field of Search .......................................... 549/10

(56) References Cited

U.S. PATENT DOCUMENTS

| | | |
|---|---|---|
| 2,799,685 A | 7/1957 | Frensch et al. |
| 3,251,856 A | 5/1966 | Schlichting |

FOREIGN PATENT DOCUMENTS

| | | |
|---|---|---|
| DE | 2505707 | 8/1976 |

OTHER PUBLICATIONS

Chemical Abstract No. 100: 134245a.
Chemical Abstract No. 107: 91836u.
Chemical Abstract No. 94: 151865c.
Chenical Abstract No. 122: 180980.
English translation of Kuhne et al., Mater Org. vol. 18, No. 2, pp. 81–91 (1983).
Akhter and Siddiqui, Kar. Univ. J. Sc., vol. 13, No. 2, pp. 191–197 (1985).
Beit et al., Int. J. Environ. Stud., vol. 16, No. 3–4, pp. 171–180 (1981).
Ceron and Camera, J. Environ. Sci. Health, vol. B30, No. 2, pp. 221–232 (1995).

Primary Examiner—Bernard Dentz
(74) Attorney, Agent, or Firm—Greenblum & Bernstein, P.L.C.

(57) ABSTRACT

A process for the stereoselective preparation of insecticide 6,7,8,9,10,10-hexahalo-1,5,5a,6,9,9a-hexahydro-6,9-methano-2,4,3-benzodioxathiepin-3-oxide of the general formula I:

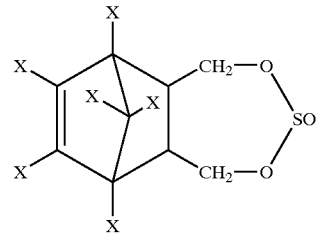

Formula I wherein X is a halogen such as fluorine, chlorine or bromine. The process comprises reacting 1,4,5,6,7,7-hexahalo-5-norbornene-2,3-dimethanol of the general formula IV:

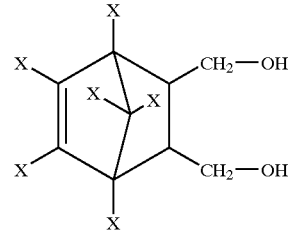

Formula IV wherein X is as defined above, with a cyclic sulfite ring forming reagent optionally in an inert organic solvent at ambient to 139° C., wherein the reaction is carried out in the presence of a stereo isomer directing agent comprising an isomer of the compound of the formula I different from the desired isomer. The molar ratio of the stereoisomer directing agent to the dimethanol compound of the formula IV is at least 0.07.

6 Claims, No Drawings

PROCESS FOR THE STEREOSELECTIVE PREPARATION OF INSECTICIDE 6,7,8,9,10-10-HEXAHALO-1,5,5A,6,9,9A-HEXADRO-6,9-METHANO-2,4,3-BENZODIOXATHIEPIN-3-OXIDE

CROSS REFERENCES TO RELATED APPLICATIONS

This application claims the benefit of PCT/IN01/00092, in the name of Ashwin Champraj Shroff, entitled "A Process For The Stereoselective Preparation Of Insecticide 6,7,8,9,10-10-Hexahalo-1,5,5A,6,9,9A-Hexahydro-6,9-Methano-2,4,3-Benzodioxathiepin-3-Oxide," filed on Apr. 24, 2001.

A process for the stereoselective preparation of insecticide 6,7,8,9,10,10-hexahalo-1,5,5a,6,9,9a-hexahydro-6,9-methano-2,4,3-benzodioxathiepin-3-oxide.

6,7,8,9,10,10-hexahalo-1,5,5a,6,9,9a-hexahydro-6,9-methano-2,4,3-benzodioxathiepin-3-oxide are of the formula I:

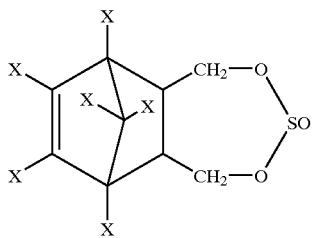

Formula I wherein X may be a halogen such as fluorine, chlorine or bromine.

PRIOR ART

U.S. Pat. No. 2,799,685 describes unsaturated polycyclic sulfites of the general formula II:

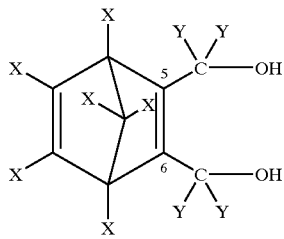

Formula II wherein X may be hydrogen or halogen or alkyl group and Y may be hydrogen or alkyl group, and their derivatives containing two hydrogen atoms in 5,6-positions. These compounds are reported to exhibit insecticidal activity. The process for the preparation of these compounds comprises heating a diol of the general formula III:

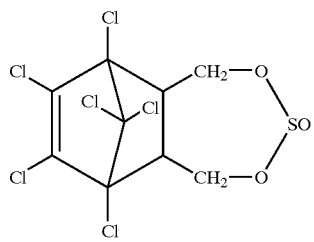

Formula III wherein X and Y are each as defined above, with thionyl chloride under heating optionally in an inert organic solvent. The product is reported to be a mixture of two isomers. The desired isomer may be resolved from the mixture, for instance by fractional crystallisation using petroleum ether.

U.S. Pat. No. 3,251,856 describes a process for the resolution/separation of the two isomers viz α and β-isomers of 6,7,8,9,10,10-hexahalo-1,5,5a,6,9,9a-hexahydro-6,9-methano-2,4,3-benzodioxathiepin-3-oxide, commonly known as endosulfan of the formula IA:

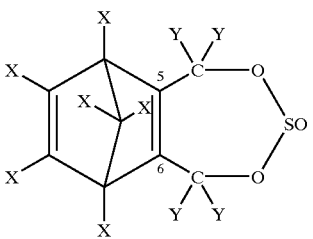

Formula IA

The resolution process comprises contacting the endosulfan isomeric mixture with a halogenated hydrocarbon solvent at 40–50° C. followed by cooling the mixture to 20–25° C. The resulting insoluble portion in the mixture is reported to predominantly contain the high melting isomer viz β-isomer of endosulfan whereas the solution portion when subjected to evaporation results in a residue which is reported to predominantly contain the low melting isomer viz α-isomer of endosulfan. The α and β-isomers so obtained may be purified by crystallisation from alcohol.

Both the isomers of endosulfan are reported to exhibit different insecticidal properties. For instance, in short exposure periods, α-endosulfan is more effective against flies than β-endosulfan. In the case of fruit flies *Drosophila melanogaster*, the killing times ($LT_{50}$) with the use of α-endosulfan and β-endosulfan are in the ratio 1:3 respectively. Insecticidal effectiveness or efficacy of α-endosulfan against wood boring insects is more as compared to β-endosulfan. Insecticidal effectiveness limit per $m^3$ wood with the larvae of the house longhorn beetle *Hylotupes bajulus L* is more in the case of β-endosulfan as compared to α-endosulfan (Mater. Org. 1983, 18(2), 81–91, Kuelune Helmut et al; CA 100: 134245a). Both the isomers differ in insecticidal persistence and biodegradability. α-Endosulfan decomposes rapidly by soil microorganisms when compared to β-endosulfan (Karachi Univ J. Sci; 1985, 13(2), 191–7, Akhtar Shahida et al; CA 107: 91836u). α-Endosulfan is degradable by both bacteria and fungi, whereas β-endosulfan is degradable mainly by bacteria (Int. J Environ. Stud, 1981, 16 (3–4), 171–80, El Beit, I O D et al; CA 94: 151865c). β-endosulfan has greater half life than α-endosulfan under varying environmental conditions (J. Environ. Sci. Health, Part B, 1995, B30 (2), 221–32, Ceron J J et al; CA 122: 180980p). Therefore, treatment with β-endosulfan is particularly preferred to achieve desired efficacy over a long term.

The α and β-isomers of endosulfan are reported to be obtained in the average isomeric ratio of about 2:1 (U.S. Pat. No. 3,251,856). Due to the different in the physical, chemical and biological properties of α and β-endosulfan and α and β-benzodioxathiepin compounds in general, it is advantageous to have increased quantity of the desired stereoisomer in the isomeric mixture depending upon the intended specific application of the benzodioxathiepin compound. In order to obtain required quantity of a desired isomer of the benzodioxathiepin compound, correspondingly large quantities of the substrate viz the diol compound is required. Therefore, the above process is uneconomical. Besides, it also generates the undesired isomer in the ratio 2:1 and its efficiency is low.

OBJECTS OF THE INVENTION

An object of the invention is to provide a process for the stereoselective preparation of 6,7,8,9,10,10-hexahalo-1,5, 5a,6,9,9a-hexahydro-6,9-methano-2,4,3-benzodioxathiepin-3-oxide having insecticidal activity, which results in increased quantity of the desired stereoisomer in high purity without using additional quantity of starting material.

Another object of the invention is to provide a process for the stereoselective preparation of 6,7,8,9,10,10-hexahalo-1, 5,5a,6,9,9a-hexahydro-6,9-methano-2,4,3-benzodioxathiepin-3-oxide having insecticidal activity, which is economical.

Another object of the invention is to provide a process for the stereoselective preparation of 6,7,8,9,10,10-hexahalo-1, 5,5a,6,9,9a-hexahydro-6,9-methano-2,4,3-benzodioxathiepin-3-oxide having insecticidal activity, which is efficient.

Another object of the invention is to provide a process for the stereoselective preparation of 6,7,8,9,10,10-hexahalo-1, 5,5a,6,9,9a-hexahydro-6,9-methano-2,4,3-benzodioxathiepin-3-oxide having insecticidal activity, without using any foreign reagent which may introduce impurity to the product.

DESCRIPTION OF INVENTION

According to the invention there is provided a process for the stereoselective preparation of insecticide 6,7,8,9,10,10-hexahalo-1,5,5a,6,9,9a-hexahydro-6,9-methano-2,4,3-benzodioxathiepin-3-oxide of the general formula I:

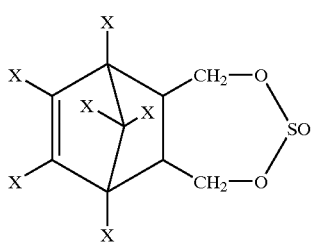

Formula I wherein X is a halogen such as fluorine, chlorine or bromine, comprising reacting 1,4,5,6,7,7-hexahalo-5-norbornene-2,3-dimethanol of the general formula IV:

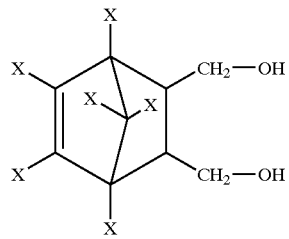

Formula IV wherein X is as defined above, with a cyclic sulfite ring forming reagent optionally in an inert organic solvent at ambient to 139° C., wherein the reaction is carried out in the presence of a stereoisomer directing agent comprising an isomer of the compound of the formula I different from the desired isomer, the molar ratio of the stereoisomer directing agent to the dimethanol compound of the formula IV being at least 0.07.

Preferably the process comprises preparation of α-isomer of the benzodioxathiepin-3-oxide compound in which its β-isomer is used as the stereoisomer directing agent, in the molar ratio of 0.2 to 0.8 to the dimethanol compound of the formula IV. Preferably the process comprises preparation of β-isomer of the benzodioxathiepin-3-oxide compound in which its α-isomer is used as the stereoisomer directing agent, in the molar ratio of 1.7 to 4.3 to the dimethanol compound.

Preferably the process comprises preparation of α-isomer of 6, 7, 8, 9, 10, 10-hexachloro-1, 5, 5a, 6, 9, 9a-hexahydro-6, 9-methano-2,4,3-benzodioxathiepin-3-oxide ie endosulfan (compound of the formula I wherein X is chlorine) in which its β-isomer is used as the stereoisomer directing agent, the molar ratio of the β-isomer of endosulfan to 1,4,5,6,7,7-hexachloro-5-norbornene-2,3-dimethanol ie endosulfandiol (compound of the formula IV wherein X is chlorine) being 0.2 to 0.8. Preferably the process comprises preparation of β-isomer of 6,7,8,9,10,10-hexahalo-1,5,5a,6, 9,9a-hexahydro-6,9-methano-2,4,3-benzodioxathiepin-3-oxide ie endosulfan (compound of the formula I wherein X is chlorine) in which its α-isomer is used as the stereoisomer directing agent, molar ratio of the α-isomer of endosulfan to 1,4,5,6,7,7-hexachloro-5-norbornene-2,3-dimethanol ie endosulfandiol (compound of the formula IV wherein X is chlorine) being 1.7 to 4.3.

The cyclic sulfite ring forming agent is preferably thionyl chloride.

The inert organic solvent may be aromatic hydrocarbon such as toluene or isomer of xylene such as o-xylene, m-xylene p-xylene or mixture thereof, aliphatic hydrocarbon such as n-hexane, octane, chlorinated aliphatic or aromatic hydrocarbon such as 1,2-dichloroethane, 1,1,2-trichloroethane, carbontetrachloride or trichloromethane or cyclo aliphatic hydrocarbon such as cyclohexane or any such solvent of petroleum origin. Preferably, toluene, o-xylene or carbontetrachloride is used as the solvent. When an inert organic solvent is not used, the reaction may be carried out in the presence of excess of cyclic sulfite ring forming reagent.

The stereoisomer directing agent is separated from the reaction mass in known manner, for instance by the method disclosed in U.S. Pat. No. 3,251,856.

According to the invention practically only one of the desired isomers viz α or β isomer is selectively prepared in high purity by using the stereoisomer directing agent, depending upon the specific intended use thereof. For instance, to give treatments lasting a longer duration, compound of the formula I wherein X is chlorine ie endosulfan, enriched with the β-isomer is prepared; whereas for treating wood α-endosulfan enriched product is prepared. Thus the process of the invention results in a product enriched with the desired isomer. Besides, for a given amount of the starting material the process produces the compound of the formula I enriched with the desired isomer practically devoid of the undesired isomer without consuming additional quantities of the starting material. Therefore, the process is economical and efficient. Since no foreign reagent is used in the reaction and the process uses the α or β isomer of the compound of the formula I itself as the stereoisomer directing agent for the preparation of β or α isomer respectively, formation of impurities is avoided. The stereoisomer directing agent in the product mixture is recovered and reused.

The following experimental examples are illustrative of the invention but not limitative of the scope thereof.

Selectively of the process for α-endosulfan/β-endosulfan was calculated by the equation:

$$\text{Selectivity} = \frac{\alpha\text{-endosulfan}/\beta\text{-endosulfan obtained }(g)}{\text{endosulfan product }(g)} \times 100$$

The weight of endosulfan product was computer after subtracting the weight of SIDC-A/SIDC-B added in the reaction mixture from the weight of the product mixture.

Example 1

Endosulfandiol (250 g, 0.693 mole), carbontetrachloride (750 ml) and β-endosulfan [stereoisomer directing agent (SIDC-A), 20 g, 0.049 mole, mole ratio of SIDC-A:endosulfandiol:: 0.071] were heated to 65° C. with stirring. Thionyl chloride (55 ml, 0.7556 mole) was added to the reaction mixture and the reaction mixture was heated to 75° C. for 2 hours. HCl generated during the reaction was scrubbed with alkali solution. The reaction mass was cooled to 30° C. Excess thionyl chloride was neutralised with dilute aqueous 6.5% weight/weight soda ash solution to pH 6.5. The aqueous layer was discarded. From the organic layer, carbontetrachloride was distilled off under reduced pressure. The product mixture weighing 290 g was analysed for α-endosulfan content by Gas Chromatography (GC) and was found to contain 202.7 g of α-endosulfan. SIDC-A in the product mixture was separated from the α-endosulfan as per the procedure of U.S. Pat. No. 3,251,856 and reused. The selectivity of the process for α-endosulfan was found to be 75.07%.

Examples 2 to 12

The procedure of Example 1 was followed using different quantities of SIDC-A and the results were as in the following Table 1:

TABLE 1

| Eg No | Endo-sulfan-diol (mol) | SIDC-A (mol) | SIDC-A:Endo-sulfandiol mole ratio | Endo-sulfan product (g) | α-Endo-sulfan (g) | Selectivity for α-endosulfan |
|---|---|---|---|---|---|---|
| 2 | 0.693 | 0 | 0 | 273 | 190.6 | 69.81 |
| 3 | 0.693 | 0.098 | 0.141 | 275 | 220.8 | 80.3 |
| 4 | 0.693 | 0.147 | 0.212 | 271 | 235.7 | 86.97 |
| 5 | 0.693 | 0.197 | 0.284 | 271 | 245.7 | 90.66 |
| 6 | 0.693 | 0.246 | 0.355 | 271 | 264.2 | 97.49 |
| 7 | 0.693 | 0.295 | 0.426 | 277 | 277.1 | 100.0 |
| 8 | 0.693 | 0.344 | 0.496 | 269 | 266.7 | 99.14 |
| 9 | 0.693 | 0.399 | 0.576 | 272 | 267.8 | 98.46 |
| 10 | 0.693 | 0.442 | 0.638 | 272 | 266.7 | 98.05 |

TABLE 1-continued

| Eg No | Endo-sulfan-diol (mol) | SIDC-A (mol) | SIDC-A:Endo-sulfandiol mole ratio | Endo-sulfan product (g) | α-Endo-sulfan (g) | Selectivity for α-endosulfan |
|---|---|---|---|---|---|---|
| 11 | 0.693 | 0.491 | 0.709 | 273 | 264.4 | 96.85 |
| 12 | 0.693 | 0.540 | 0.779 | 274 | 271.2 | 98.98 |

Example 13 to 24

The procedure of Examples 1 to 12 were followed using o-xylene as the solvent and the results were as in the following Table 2:

TABLE 2

| Eg No | Endo-sulfan-diol (mol) | SIDC-A (mol) | SIDC-A:Endo-sulfandiol mole ratio | Endo-sulfan product (g) | α-Endo-sulfan (g) | Selectivity for α-endosulfan (%) |
|---|---|---|---|---|---|---|
| 13 | 0.693 | 0 | 0 | 273 | 179.00 | 65.57 |
| 14 | 0.693 | 0.049 | 0.071 | 273 | 191.33 | 70.08 |
| 15 | 0.693 | 0.098 | 0.141 | 273 | 204.86 | 75.04 |
| 16 | 0.693 | 0.147 | 0.212 | 273 | 217.45 | 79.65 |
| 17 | 0.693 | 0.197 | 0.284 | 273 | 230.69 | 84.50 |
| 18 | 0.693 | 0.246 | 0.355 | 273 | 243.94 | 89.36 |
| 19 | 0.693 | 0.295 | 0.426 | 273 | 256.0 | 93.77 |
| 20 | 0.693 | 0.344 | 0.496 | 273 | 270.02 | 98.91 |
| 21 | 0.693 | 0.399 | 0.576 | 273 | 269.76 | 98.81 |
| 22 | 0.693 | 0.442 | 0.638 | 272 | 269.17 | 98.96 |
| 23 | 0.693 | 0.491 | 0.709 | 273 | 270.79 | 99.19 |
| 24 | 0.693 | 0.510 | 0.779 | 276 | 271.41 | 98.34 |

Examples 25 to 36

The procedure of Examples 1 to 12 were followed using toluene as the solvent and the results were as in the following Table 3:

TABLE 3

| Eg No | Endo-sulfan-diol (mol) | SIDC-A (mol) | SIDC-A:Endo-sulfandiol mole ratio | Endo-sulfan product (g) | α-Endo-sulfan (g) | Selectivity for α-endosulfan (%) |
|---|---|---|---|---|---|---|
| 25 | 0.693 | 0 | 0 | 273 | 175.8 | 64.4 |
| 26 | 0.693 | 0.049 | 0.071 | 273 | 188.4 | 69.0 |
| 27 | 0.693 | 0.098 | 0.141 | 273 | 201.9 | 74.0 |
| 28 | 0.693 | 0.147 | 0.212 | 273 | 213.8 | 78.3 |
| 29 | 0.693 | 0.197 | 0.284 | 273 | 227.3 | 83.3 |
| 30 | 0.693 | 0.246 | 0.355 | 273 | 241.0 | 88.3 |
| 31 | 0.693 | 0.295 | 0.426 | 273 | 252.3 | 92.4 |
| 32 | 0.693 | 0.344 | 0.496 | 273 | 265.6 | 97.3 |
| 33 | 0.693 | 0.399 | 0.576 | 273 | 269.8 | 98.8 |
| 34 | 0.693 | 0.442 | 0.638 | 273 | 265.2 | 97.2 |
| 35 | 0.693 | 0.491 | 0.709 | 273 | 270.8 | 99.2 |
| 36 | 0.693 | 0.540 | 0.779 | 273 | 269.8 | 98.8 |

Examples 37 to 41

The procedure of example 8 was followed varying the temperatures and the results were as shown in the following Table 4.

TABLE 4

| Example No | 37 | 38 | 39 | 40 | 41 |
|---|---|---|---|---|---|
| Endosulfandiol (mole) | 0.693 | 0.693 | 0.693 | 0.693 | 0.693 |
| SIDC-A (mole) | 0.344 | 0.344 | 0.344 | 0.344 | 0.344 |
| SIDC-A to Endosulfandiol mole ratio | 0.497 | 0.497 | 0.497 | 0.497 | 0.497 |
| Reaction temperature (° C.) | 15 | 25 | 35 | 50 | 75 |
| Reaction time (hrs) | 8 | 6 | 4 | 2 | 1 |
| Endosulfan product (gms) | 269 | 268 | 270 | 269 | 266 |
| α-Endosulfan content in the product mixture (gms) | 266.6 | 265.2 | 266.9 | 266.6 | 265.5 |
| Selectivity for α-Endosulfan (%) | 99.10 | 98.95 | 98.85 | 99.10 | 99.81 |

Example 42

Endosulfandiol (250 g, 0.69 mole), carbotetrachloride (750 ml) and α-endosulfan [stereoiosomer directing agent (SIDC-B), 100 g, 0.25 mole, SIDC-B: endosulfandiol:: 0.355] were heated to 65° C. with stirring. Thionyl chloride (55 ml, 0.7556 mole) was added to the reaction mixture and the reaction mixture was heated to 75° C. for 2 hours. HCl generated during the reaction was scrubbed with alkali solution. The reaction mass was cooled to 30° C. Excess thionyl chloride was neutralised with dilute aqueous 6.5% weight/weight soda ash solution to pH 6.5. The aqueous layer was discarded. From the organic layer, carbontetrachloride was distilled off under reduced pressure. The product mixture weighing 347 g was analysed for β-endosulfan content by Gas Chromatography (GC) and was found to contain 106.9 g of β-endosulfan. SIDC-B in the product mixture was separated from the β-endosulfan as per the procedure of U.S. Pat. No. 3,251,856 and reused. The selectivity of the process for β-endosulfan was found to be 39.01%.

Examples 43 to 53

The procedure of Example 42 was followed with varying quantities of SIDC-B and the results were as in the following Table 5:

TABLE 5

| Eg No | Endo-sulfan-diol (mol) | SIDC-B (mol) | SIDC-B:endo-sulfandiol mole ratio | Endo-sulfan product (g) | β-Endo-sulfan (g) | Selectivity for β-endosulfan (%) |
|---|---|---|---|---|---|---|
| 43 | 0.693 | 0 | 0 | 273 | 77.8 | 28.5 |
| 44 | 0.693 | 0.49 | 0.709 | 274 | 135.3 | 49.37 |
| 45 | 0.693 | 0.74 | 1.064 | 274 | 163.9 | 59.82 |
| 46 | 0.693 | 0.98 | 1.418 | 275 | 193.0 | 70.18 |
| 47 | 0.693 | 1.23 | 1.773 | 273 | 220.8 | 80.90 |
| 48 | 0.693 | 1.47 | 2.127 | 273 | 249.3 | 91.32 |
| 49 | 0.693 | 1.72 | 2.482 | 273 | 272.0 | 98.91 |
| 50 | 0.693 | 1.97 | 2.836 | 274 | 273.7 | 99.89 |
| 51 | 0.693 | 2.21 | 3.191 | 274 | 272.7 | 99.53 |
| 52 | 0.693 | 2.46 | 3.545 | 275 | 274.0 | 99.64 |
| 53 | 0.693 | 2.95 | 4.255 | 274 | 273.7 | 99.89 |

Examples 54 to 65

The procedure of Examples 42 to 53 were followed using o-xylene as the solvent and the results were in the following Table 6:

TABLE 6

| Eg No | Endo-sulfan-diol (mol) | SIDC-B (mol) | SIDC-B:Endo-sulfandiol mole ratio | Endo-sulfan product (g) | β-Endo-sulfan (g) | Selectivity for β-endosulfan (%) |
|---|---|---|---|---|---|---|
| 54 | 0.693 | 0 | 0 | 274 | 88.2 | 32.19 |
| 55 | 0.693 | 0.25 | 0.355 | 273 | 121.3 | 44.43 |
| 56 | 0.693 | 0.49 | 0.709 | 274 | 155.0 | 56.57 |
| 57 | 0.693 | 0.74 | 1.064 | 274 | 188.4 | 68.75 |
| 58 | 0.693 | 0.98 | 1.418 | 274 | 221.8 | 80.93 |
| 59 | 0.693 | 1.23 | 1.773 | 275 | 255.5 | 92.90 |
| 60 | 0.693 | 1.47 | 2.217 | 273 | 271.7 | 99.52 |
| 61 | 0.693 | 1.72 | 2.482 | 273 | 272.4 | 99.78 |
| 62 | 0.693 | 1.97 | 2.836 | 275 | 274.0 | 99.64 |
| 63 | 0.693 | 2.21 | 3.191 | 276 | 273.2 | 99.00 |
| 64 | 0.693 | 2.46 | 3.545 | 275 | 274.0 | 99.64 |
| 65 | 0.693 | 2.95 | 4.255 | 274 | 272.4 | 99.42 |

Examples 66 to 77

The procedure of Example 42 to 53 were followed using toluene as the solvent and the results were as in the following Table 7:

TABLE 7

| Eg No | Endo-sulfan-diol (mol) | SIDC-B (mol) | SIDC-B:Endo-sulfandiol mole ratio | Endo-sulfan product (g) | β-Endo-sulfan (g) | Selectivity for β-endosulfan (%) |
|---|---|---|---|---|---|---|
| 66 | 0.693 | 0 | 0 | 273 | 84.6 | 31.00 |
| 67 | 0.693 | 0.25 | 0.355 | 274 | 117.3 | 42.81 |
| 68 | 0.693 | 0.49 | 0.709 | 274 | 149.6 | 54.59 |
| 69 | 0.693 | 0.74 | 1.064 | 274 | 181.9 | 66.38 |
| 70 | 0.693 | 0.98 | 1.418 | 275 | 214.9 | 78.15 |
| 71 | 0.693 | 1.23 | 1.773 | 273 | 246.2 | 90.18 |
| 72 | 0.693 | 1.47 | 2.217 | 273 | 271.7 | 99.52 |
| 73 | 0.693 | 1.72 | 2.482 | 275 | 273.0 | 99.27 |
| 74 | 0.693 | 1.97 | 2.836 | 274 | 273.7 | 99.91 |
| 75 | 0.693 | 2.21 | 3.191 | 274 | 272.8 | 99.55 |
| 76 | 0.693 | 2.46 | 3.545 | 275 | 274.0 | 99.64 |
| 77 | 0.693 | 2.95 | 4.255 | 274 | 273.8 | 99.93 |

Examples 78–82

The procedure of example 61 was followed varying the temperature and the results were as shown in the following Table 8.

TABLE 8

| Example No | 78 | 79 | 80 | 81 | 82 |
|---|---|---|---|---|---|
| Endosulfandiol (mole) | 0.693 | 0.693 | 0.693 | 0.693 | 0.693 |
| SIDC-B (mole) | 1.72 | 1.72 | 1.72 | 1.72 | 1.72 |
| SIDC-B to Endosulfandiol mole ratio | 2.482 | 2.482 | 2.482 | 2.482 | 2.482 |
| Reaction temperature (° C.) | 15 | 25 | 35 | 50 | 75 |
| Reaction time (hrs) | 8 | 6 | 4 | 2 | 1 |
| Endosulfan product (gms) | 274 | 272.9 | 273.2 | 274 | 273 |
| β-Endosulfan content in the product mixture (gms) | 270.9 | 270.0 | 271.0 | 270.8 | 267.5 |
| Selectivity for β-Endosulfan (%) | 98.89 | 98.94 | 99.19 | 98.83 | 97.98 |

The results of Examples 1 to 36 as shown in Tables 1 to 3 clearly show that selectively of the process for α-endosulfan depends on the molar ratio of SIDC-A to endosulfandiol. Similarly the results of Examples 42 to 77 as shown in Tables 5 to 7 clearly show that selectively of the process for β-endosulfan depends on the molar ratio of SIDC-B to endosulfandiol. The results of Examples 37 to 41 and 78 to 82 as shown in Tables 4 and 8 clearly indicate that temperature has practically no effect on the selectivity of the process for α-endosulfan or β-endosulfan.

What is claimed is:

1. A process for the stereoselective preparation of insecticide 6,7,8,9,10,10-hexahalo-1,5,5a,6,9,9a-hexahydro-6,9-methano-2,4,3-benzodioxathiepin-3-oxide of the general formula I:

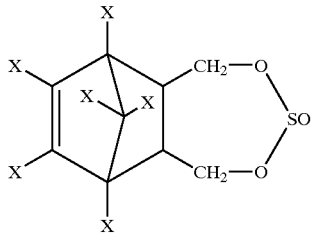

Formula I wherein X is a halogen selected from fluorine, chlorine or bromine, comprising reacting 1,4,5,6,7,7-hexahalo-5-norbornene-2,3-dimethanol of the general formula IV:

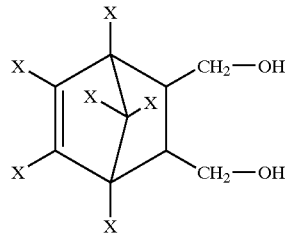

Formula IV wherein X is a halogen selected from fluorine, chlorine or bromine, with a cyclic sulfite ring forming reagent optionally in an inert organic solvent at ambient to 139° C., wherein the reaction is carried out in the presence of a stereo isomer directing agent comprising an isomer of the compound of the formula 1 different from the desired isomer, the molar ratio of the stereoisomer directing agent to the dimethanol compound of the formula IV at least 0.07.

2. A process of claim 1, for the preparation of α-isomer of the benzodioxathiepin-3-oxide compound in which its β-isomer is used as the stereo isomer directing agent in the molar ratio of 0.2 to 0.8 to the dimethanol compound.

3. A process of claim 1, for the preparation of β-isomer of the benzodioxathiepin-3-oxide compound in which its α-isomer is used as the stereo isomer directing agent in the molar ratio of 1.7 to 4.3 to the dimethanol compound.

4. A process of claim 1, for the preparation of α-isomer of 6, 7, 8, 9, 10, 10-hexahalo-1, 5, 5a,6, 9, 9a-hexahydro-6, 9-methano-2,4,3-benzodioxathiepin-3-oxide or endosulfan in which its β-isomer is used as the stereoisomer directing agent, the molar ratio of the β-isomer of endosulfan to 1,4,5,6,7,7-hexachloro-5-norbornene-2,3-dimethanol or endosulfandiol being 0.2 to 0.8.

5. A process of claim 1, for the preparation of β-isomer of 6,7,8,9,10,10-hexahalo-1,5,5a,6,9,9a-hexahydro-6,9-methano-2,4,3-benzodioxathiepin-3-oxide or endosulfan in which its α-isomer is used as the stereoisomer directing agent, molar ratio of the α-isomer of endosulfan to 1,4,5,6, 7,7-hexachloro-5-norbornene-2,3-dimethanol or endosulfandiol being 1.7 to 4.3.

6. A process of claim 1, wherein the cyclic sulfite ring forming agent is thionyl chloride.

* * * * *

UNITED STATES PATENT AND TRADEMARK OFFICE
CERTIFICATE OF CORRECTION

PATENT NO. : 6,831,179 B2
DATED : December 14, 2004
INVENTOR(S) : A. Shroff et al.

It is certified that error appears in the above-identified patent and that said Letters Patent is hereby corrected as shown below:

<u>Title page,</u>
Item [54], Title, "HEXADRO" should be -- HEXAHYDRO --.

<u>Column 10,</u>
Lines 34 and 41, "hexahalo" should be -- hexachloro --.

Signed and Sealed this

Ninth Day of August, 2005

JON W. DUDAS
*Director of the United States Patent and Trademark Office*